United States Patent [19]

Martel et al.

[11] Patent Number: 5,295,968
[45] Date of Patent: Mar. 22, 1994

[54] STYLET WIRE ASSEMBLY

[75] Inventors: Mark C. Martel; John Karpiel, both of Winston-Salem, N.C.

[73] Assignee: Wilson-Cook Medical Inc., Winston-Salem, N.C.

[21] Appl. No.: 932,321

[22] Filed: Aug. 19, 1992

[51] Int. Cl.$^5$ .............................................. A61M 5/00
[52] U.S. Cl. .................................... 604/164; 604/167
[58] Field of Search ........................ 604/164, 167, 170

[56] References Cited

U.S. PATENT DOCUMENTS

| | | | |
|---|---|---|---|
| 3,766,916 | 10/1973 | Moorehead et al. | 604/167 |
| 3,851,647 | 12/1974 | Monestere, Jr. et al. | 604/167 |
| 4,073,297 | 2/1978 | Kopp | 604/164 |
| 4,096,860 | 6/1978 | McLaughlin | 604/167 |
| 4,581,019 | 4/1986 | Curelaru et al. | 604/164 |
| 4,659,328 | 4/1987 | Potter et al. | |
| 4,791,937 | 12/1988 | Wang | 604/164 |
| 4,798,593 | 1/1989 | Iwatschenko | |
| 4,863,431 | 9/1989 | Vaillancourt | 604/120 |
| 4,950,257 | 8/1990 | Hibbs et al. | 604/167 |
| 5,021,044 | 6/1991 | Sharkawy | 604/164 |
| 5,026,351 | 6/1991 | Dizon | |
| 5,078,688 | 1/1992 | Lobodzinski et al. | 604/164 |
| 5,125,904 | 6/1992 | Lee | 604/164 |
| 5,151,087 | 9/1992 | Jonkman | 604/164 |

*Primary Examiner*—Paul J. Hirsch
*Attorney, Agent, or Firm*—Woodard, Emhardt, Naughton, Moriarty & McNett

[57] ABSTRACT

A stylet wire assembly is disclosed which sealingly engages the proximal end of a medical catheter, and allows the unobstructed injection or evacuation of fluids into or from a patient's body through the catheter while the stylet wire is in place therein. The disclosed assembly includes a stylet wire and a housing. The housing has a catheter fluid communication port at its distal end and anchors the stylet wire into its closed proximal end with the stylet wire extending through the catheter fluid communication port at the distal end of the housing. This anchoring is accomplished by means of a plug which has been injection molded about the crimped proximal end of the stylet wire and bonded to the distal end of the remainder of the housing. An external fluid communication port allows for fluid communication into and out of said housing in transverse orientation relative to the axis of said stylet wire within said housing and distally of the anchoring of the stylet wire into the proximal end of the housing. The distal end of the housing sealingly engages the proximal end of a medical catheter in fluid communication between the catheter fluid communication port of the housing and the fluid conduit of the catheter by means of the combined effect of a female threaded portion which advances over the end of the catheter and an inner sealing tubular portion which advances within the fluid conduit of the catheter. A fluid conduit provides fluid communication within the housing between the catheter fluid communication port and the external fluid communication port. Upon removal of the stylet wire assembly, the proximal end of the medical catheter can be connected directly to an infusion/evacuation tube without the need for sealing the second port of the standardly used T-fitting.

4 Claims, 2 Drawing Sheets

STYLET WIRE ASSEMBLY

BACKGROUND OF THE INVENTION

The present invention relates generally to devices which provide stiffening reinforcement for catheters and other medical probes for placement into the body of a patient. In particular, this invention relates to stylet wire assemblies which are to be maintained in place within a catheter while the catheter is being used for fluid infusion or evacuation.

Many medical procedures require the insertion of a catheter into the body. Catheters are usually made of flexible or pliable material to facilitate insertion into and advancement within the body. These devices, however, sometimes lack sufficient rigidity when used in certain situations and require reinforcement in order to maintain their desired structures. Stylet wires used to stiffen catheters for this purpose are well known in the prior art.

In some situations, it is necessary to maintain the stylet wire in place while the catheter is being used for fluid infusion or evacuation. When this is done, access into and through the fluid conduit of the catheter must be kept open while the stylet is in place within the catheter. This is commonly accomplished by using a T-fitting which connects to the proximal end of the catheter. With the stylet wire inserted into the catheter through an axial opening in the T-fitting, fluids can be inserted and/or evacuated through the T-fitting's transverse port. The fitting of catheters with T-fittings for this purpose adds to the cost of manufacturing these devices, and sometimes unnecessarily so, since they do not always need to be used in conjunction with a stylet wire in place. Also, when such a catheter fitted with a T-fitting is used for infusion or evacuation without a stylet wire in place, the user of the device must first be sure to cap the second port on the T-fitting. If the cap is not properly placed, or is forgotten, fluids may leak or even spurt out through this unsealed port causing, at the least, inconvenience, and possibly even, failure of the procedure.

Prior art devices have also been designed which have incorporated into the stylet wire assembly itself the capability to provide fluid communication through the catheter while the stylet wire is in place within the catheter. U.S. Pat. No. 5,026,351 to Dizon discloses an IV stylet catheter having a housing attached to a stylet which is received into the catheter. The Dizon device allows fluid to be injected through the housing and into the catheter with the device placed therein. U.S. Pat. No. 4,659,328 to Potter et al. and U.S. Pat. No. 4,798,593 to Iwatschenko also disclose structures which incorporate a fluid communication fitting into a stylet wire assembly to allow for fluid communication through a catheter while the stylet wire is in place. In each of these prior art devices, fluid communication is necessarily constricted by the anchoring of the wire within the housing of the assembly, as any fluids must pass the anchoring structure in order to enter or exit the assembly. The anchorage of the wire in these devices thus presents an obstruction to the flow of fluid through the catheter, thereby preventing the catheter from functioning as optimally as possible.

SUMMARY OF THE INVENTION

The present invention provides a new and unique stylet wire assembly which overcomes the limitations of the prior art. As shown in the preferred embodiment described herein, there is provided an integral stylet wire assembly which sealingly engages the proximal end of a medical catheter. The stylet wire assembly allows the unobstructed injection or evacuation of fluids into or from a patient's body through the catheter while the stylet wire is in place therein. Upon removal of the stylet wire assembly, the proximal end of the medical catheter can be connected directly to an infusion/evacuation tube without the need for sealing the second port of the standardly used T-fitting.

BRIEF DESCRIPTION OF THE DRAWINGS

In FIGS. 2 and 3, the location of internal passageways of stylet wire assembly 10 and catheter 20 have been shown in dashed form, as well as the positioning of stylet wire 11 therein.

FIG. 4 illustrates external detailing in lieu of the internal detailing shown in FIGS. 2 and 3, including longitudinal ridges 19 for gripping and handling, and also shows the placement of infusion/evacuation tube 30 onto external fluid communication port 15.

DESCRIPTION OF THE PREFERRED EMBODIMENT

Figure 1:
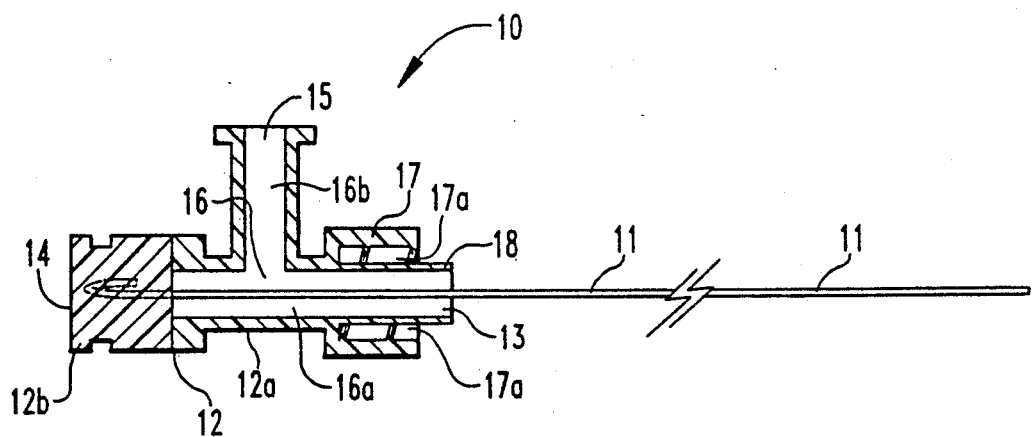
FIG. 1 is a partially fragmented cross-sectioned view of a stylet wire assembly according to the present invention.

For the purposes of promoting an understanding of the principals and operation of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to those skilled in the art to which the invention pertains.

Referring now to the drawings, and more particularly to FIG. 1, this figure is a partially fragmented cross-sectioned view of a stylet wire assembly 10 according to the present invention. Stylet wire assembly 10 includes stylet wire 11 and housing 12. Housing 12 has a catheter fluid communication port 13 at its distal end and anchors stylet wire 11 into its closed proximal end 14 with stylet wire 11 extending through catheter fluid communication port 13 at the distal end of housing 12. External fluid communication port 15 allows for fluid communication into and out of housing 12 in transverse orientation relative to the axis of stylet wire 11 within housing 12 and distally of the location of anchoring of stylet wire 11 at the closed proximal end 14 of housing 12. Fluid conduit 16 provides fluid communication within housing 12 between catheter fluid communication port 13 and external fluid communication port 15.

Housing 12 includes manifold 12a and plug 12b. Manifold 12a defines catheter fluid communication port 13 and external fluid communication port 15, and further defines fluid conduit 16 which interconnects these two ports. Fluid conduit 16 includes an axial passageway portion 16a connecting to catheter communication port 13, and also includes transverse passageway portion 16b connecting axial passageway portion 16a to external fluid communication port 15. Plug 12b has been integrally molded about the crimped proximal end portion 11a of stylet wire 11, and has been bonded to the distal end of manifold 12a to close the proximal end of housing 12 with stylet wire 11 securely anchored to plug 12b and extending through axial passageway portion 16a of fluid conduit 16 and out through catheter fluid communication port 13 at the distal end of housing 12.

Sealing engagement of housing 12 to a medical catheter is provided by female threaded portion 17 and inner sealing tubular portion 18. Female threaded portion 17 is sized to receive the proximal end of a medical catheter and to be threaded thereabout. For this purpose, female threaded portion 17 includes an internal thread 17a. Inner sealing tubular portion 18 is sized to be received within the proximal end of a catheter and, when advanced therein in combination with female threaded portion 17 being threaded thereabout, provides a secure sealing between housing 12 and the catheter to which it is to be attached.

Figure 2:
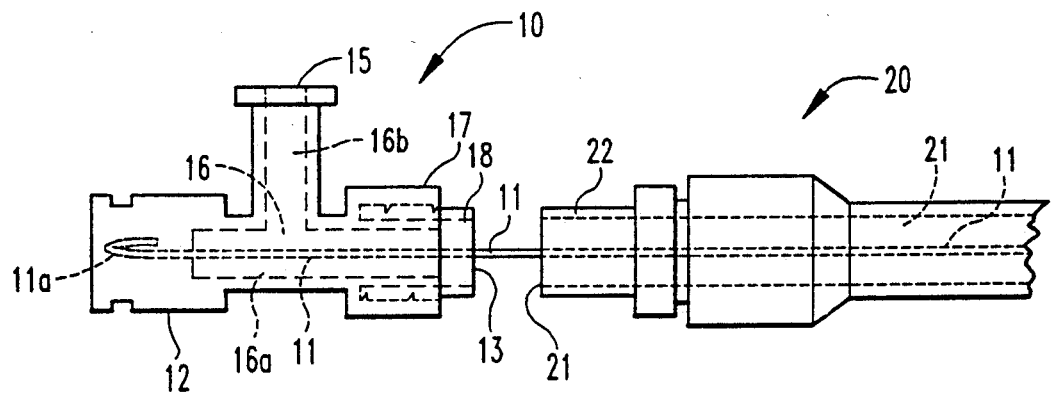
FIG. 2 is a side elevational view of the stylet wire assembly of FIG. 1, partially advanced into a medical catheter and positioned for sealing attachment thereto.
Figure 3:
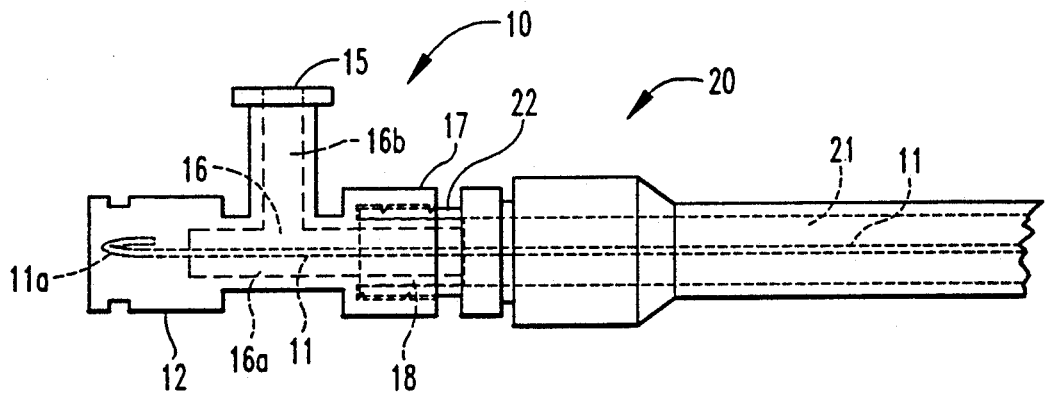
In FIG. 3, the stylet wire assembly 10 has been fully advanced into medical catheter 20, and threadedly locked into place thereon.

FIG. 2 is a side elevational view of stylet wire assembly 10, partially advanced into a medical catheter 20 and positioned to make a sealing attachment thereto. As shown in this figure, the distal end of housing 12 is in position for sealing engagement with the proximal end 22 of medical catheter 20 in fluid communication between catheter fluid communication port 13 of housing 12 and the fluid conduit 21 of catheter 20. In FIG. 3, stylet wire assembly 10 has been fully advanced into medical catheter 20, and threadedly locked into place thereon.

When attached to a catheter, as shown in FIG. 3, stylet wire assembly 10 provides for the stiffening reinforcement of the catheter, while at the same time allowing for easy unobstructed access through the catheter for the infusion or evacuation of fluids therethrough. Female threaded portion 17 and inner sealing tubular portion 18 together provide for the secure sealing attachment to the proximal end 22 of catheter 20, with catheter communication port 13 in fluid communication with the fluid conduit 21 of catheter 20, and with stylet wire 11 extending therethrough to provide stiffening reinforcement to catheter 20. Fluid conduit 16, through axial fluid passageway portion 16a and transverse fluid passageway portion 16b, provide for unobstructed fluid communication between fluid conduit 21 of catheter 20 and external fluid communication port 15. Plug 12b securely seals the proximal end 14 of housing 12, and securely anchors stylet wire 11 in place without causing an obstruction to the flow of fluid between catheter 20 and external fluid communication port 15. Stylet wire assembly is easy to construct, and is easy, convenient, and reliable to use as well.

Figure 4:
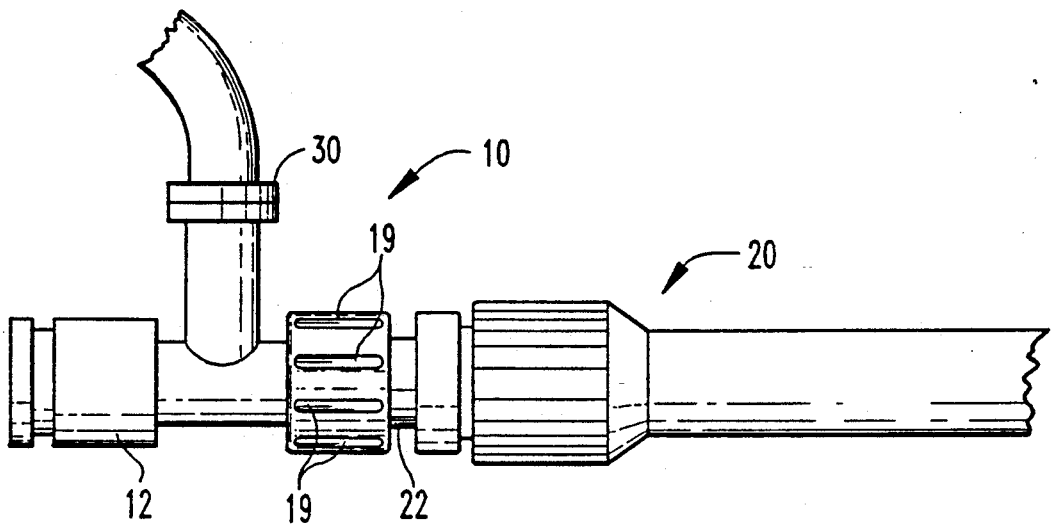
FIG. 4 shows stylet wire assembly 10 mounted onto medical catheter 20.

FIG. 4 is a side elevational view of stylet wire assembly 10 mounted onto medical catheter 20, further showing longitudinal ridges 19 which are used for gripping and handling of housing 12 to facilitate placement of housing onto medical catheter 20 and removal therefrom. FIG. 4 also shows the placement of infusion/evacuation tube 30 onto external fluid communication port 15.

Figure 5:
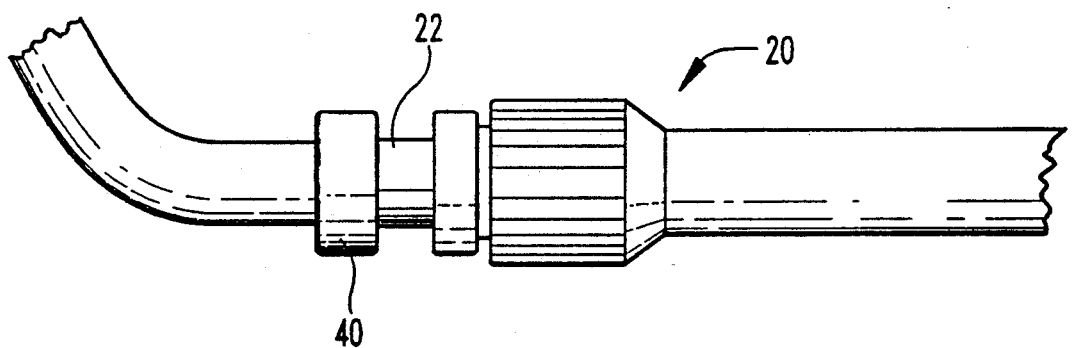
FIG. 5 shows medical catheter 20, connected to a fluid/evacuation tube 40 at its proximal end after stylet wire assembly 40 has been removed therefrom.

Upon removal of stylet wire assembly 10, the proximal end 22 of medical catheter 20 can be connected directly to an infusion/evacuation tube without the need for sealing the second port of the standardly used T-fitting. This provides an added convenience to the user of the device who would otherwise have to separately seal the secondary port of the T-fitting prior to using the catheter without a stylet wire in place. FIG. 5 shows medical catheter 20 being used in this manner, with infusion/evacuation tube 40 connected at the proximal end 22 of catheter 20 after stylet wire assembly 10 has been removed therefrom.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A stylet wire assembly for providing stiffening reinforcement to a medical catheter by placement of a stylet wire into a fluid conduit in said catheter while allowing for unobstructed fluid communication therethrough, said assembly comprising:
    a stylet wire; and
    a housing having a proximal end and a distal end, said housing including:
        a catheter fluid communication port, said catheter fluid communication port allowing for fluid communication between the distal end of said housing and the fluid conduit of said catheter;
        stylet wire anchoring means located at said proximal end of said housing for anchoring the proximal end of said stylet wire into the proximal end portion of said housing with said stylet wire extending through said catheter fluid communication port at the distal end of said housing;
        an external fluid communication port, said external fluid communication port allowing for fluid communication into and out of said housing in transverse orientation relative to the axis of said stylet wire within said housing and distally of said stylet wire anchoring means;
        sealing engagement means for sealingly engaging the distal end of said housing to the proximal end of said catheter with said catheter communication port in fluid communication with the fluid conduit of said catheter; and
        fluid conduit means for providing fluid communication within said housing between said catheter fluid communication port and said external fluid communication port.

2. The stylet wire assembly of claim 1 in which said housing includes a manifold and a plug, said manifold defining said catheter fluid communication port, said external fluid communication port, and said fluid conduit means interconnecting said ports; and wherein said stylet wire anchoring means includes said plug being integrally molded about the crimped proximal end portion of said stylet wire and bonded to the distal end of said manifold to close the proximal end of said housing with said stylet wire securely anchored to said plug and extending through said fluid conduit means and out through said catheter fluid communication port at the distal end of said housing.

3. The stylet wire assembly of claim 2 in which said fluid conduit means includes an axial passageway portion connecting to said catheter communication port, and includes a transverse passageway portion connecting said axial passageway portion to said external fluid communication port.

4. The stylet wire assembly of claim 1 in which said sealing engagement means includes a female threaded portion for advancement over the proximal end of a catheter and an inner sealing tubular portion which advances into the fluid conduit of the catheter as said female threaded portion is advanced thereover.

* * * * *